United States Patent
Gregorich et al.

(10) Patent No.: US 8,556,955 B2
(45) Date of Patent: Oct. 15, 2013

(54) ADJUSTABLE BIFURCATION CATHETER INCORPORATING ELECTROACTIVE POLYMER AND METHODS OF MAKINGS AND USING THE SAME

(75) Inventors: Daniel Gregorich, St. Louis Park, MN (US); Matt Heidner, Maple Grove, MN (US); Tracee Eidenschink, Wayzata, MN (US); Adam Jennings, Buffalo, MN (US); Yousef Alkhatib, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 13/530,400

(22) Filed: Jun. 22, 2012

(65) Prior Publication Data
US 2012/0265286 A1    Oct. 18, 2012

Related U.S. Application Data

(63) Continuation of application No. 11/591,848, filed on Nov. 2, 2006, now Pat. No. 8,206,429.

(51) Int. Cl.
*A61F 2/06* (2006.01)

(52) U.S. Cl.
USPC .......................................................... 623/1.11

(58) Field of Classification Search
USPC ............... 600/16, 30, 114, 143, 146, 152; 606/108, 153, 191; 623/1.11, 1.12, 25
See application file for complete search history.

(56) References Cited

U.S. PATENT DOCUMENTS

| | | |
|---|---|---|
| 4,309,994 A | 1/1982 | Grunwald |
| 4,769,005 A | 9/1988 | Ginsburg et al. |
| 4,774,949 A | 10/1988 | Fogarty |
| 4,896,670 A | 1/1990 | Crittenden |
| 4,905,667 A | 3/1990 | Foerster et al. |
| 4,994,071 A | 2/1991 | MacGregor |
| 5,342,387 A | 8/1994 | Summers |
| 5,387,235 A | 2/1995 | Chuter |
| 5,396,879 A | 3/1995 | Wilk et al. |
| 5,456,712 A | 10/1995 | Maginot |
| 5,476,471 A | 12/1995 | Shifrin et al. |
| 5,487,730 A | 1/1996 | Marcadis et al. |
| 5,573,520 A | 11/1996 | Schwartz et al. |

(Continued)

FOREIGN PATENT DOCUMENTS

| | | |
|---|---|---|
| CA | 2220864 | 7/1999 |
| DE | 9014845 | 2/1991 |

(Continued)

OTHER PUBLICATIONS

Zhou et al., "Actuators for the Cochlear Implant," *Synthetic Metals* 135-136 (2003) 39-40.

(Continued)

*Primary Examiner* — Ryan Severson
*Assistant Examiner* — Ashley Cronin
(74) *Attorney, Agent, or Firm* — Seager, Tufte & Wickhem LLC (57) ABSTRACT

A medical device having at least one static state, at least one activated state, and at least one active region including electroactive polymer (EAP) capable of fine electro-activated movements. The EAP movements include bending components for proper alignment, rotating components for proper fittings, making components more rigid or flexible, and increasing and decreasing the volume of components. The fine movements allow for highly versatile and adaptable medical devices.

9 Claims, 9 Drawing Sheets

(56) References Cited

U.S. PATENT DOCUMENTS

| | | |
|---|---|---|
| 5,591,228 A | 1/1997 | Edoga |
| 5,607,444 A | 3/1997 | Lam |
| 5,609,605 A | 3/1997 | Marshall et al. |
| 5,609,627 A | 3/1997 | Goicoechea et al. |
| 5,613,980 A | 3/1997 | Chauhan |
| 5,617,878 A | 4/1997 | Taheri |
| 5,632,762 A | 5/1997 | Myler |
| 5,632,763 A | 5/1997 | Glastra |
| 5,632,772 A | 5/1997 | Alcime et al. |
| 5,636,641 A | 6/1997 | Fariabi |
| 5,669,924 A | 9/1997 | Shaknovich |
| 5,669,932 A | 9/1997 | Fischell et al. |
| 5,676,697 A | 10/1997 | McDonald |
| 5,683,450 A | 11/1997 | Goicoechea et al. |
| 5,697,971 A | 12/1997 | Fischell et al. |
| 5,707,348 A | 1/1998 | Krogh |
| 5,709,713 A | 1/1998 | Evans et al. |
| 5,720,735 A | 2/1998 | Dorros |
| 5,749,825 A | 5/1998 | Fischell et al. |
| 5,749,890 A | 5/1998 | Shaknovich |
| 5,755,734 A | 5/1998 | Richter et al. |
| 5,755,735 A | 5/1998 | Richter et al. |
| 5,755,771 A | 5/1998 | Penn et al. |
| 5,755,773 A | 5/1998 | Evans et al. |
| 5,755,778 A | 5/1998 | Kleshinski |
| 5,782,906 A | 7/1998 | Marshall et al. |
| 5,800,421 A | 9/1998 | Lemelson |
| 5,824,036 A | 10/1998 | Lauterjung |
| 5,824,040 A | 10/1998 | Cox et al. |
| 5,827,320 A | 10/1998 | Richter et al. |
| 5,851,464 A | 12/1998 | Davila et al. |
| 5,855,565 A | 1/1999 | Bar-Cohen et al. |
| 5,868,777 A | 2/1999 | Lam |
| 5,893,887 A | 4/1999 | Jayaraman |
| 5,961,548 A | 10/1999 | Shmulewitz |
| 5,972,017 A | 10/1999 | Berg et al. |
| 6,013,054 A | 1/2000 | Jium |
| 6,017,324 A | 1/2000 | Tu et al. |
| 6,017,363 A | 1/2000 | Hojeibane |
| 6,030,414 A | 2/2000 | Taheri |
| 6,033,434 A | 3/2000 | Borghi |
| 6,033,435 A | 3/2000 | Penn et al. |
| 6,056,775 A | 5/2000 | Borghi et al. |
| 6,059,824 A | 5/2000 | Taheri |
| 6,068,655 A | 5/2000 | Seguin et al. |
| 6,086,611 A | 7/2000 | Duffy et al. |
| 6,093,203 A | 7/2000 | Uflacker |
| 6,096,073 A | 8/2000 | Webster et al. |
| 6,099,497 A | 8/2000 | Adams et al. |
| 6,113,579 A | 9/2000 | Eidenschink et al. |
| 6,117,117 A | 9/2000 | Mauch |
| 6,117,156 A | 9/2000 | Richter et al. |
| 6,117,296 A | 9/2000 | Thomson |
| 6,129,738 A | 10/2000 | Lashinski et al. |
| 6,142,973 A | 11/2000 | Carleton et al. |
| 6,143,002 A | 11/2000 | Vietmeier |
| 6,159,238 A | 12/2000 | Killion et al. |
| 6,165,195 A | 12/2000 | Wilson et al. |
| 6,168,621 B1 | 1/2001 | Vrba |
| 6,183,509 B1 | 2/2001 | Dibie |
| 6,203,568 B1 | 3/2001 | Lombardi et al. |
| 6,210,380 B1 | 4/2001 | Mauch |
| 6,210,429 B1 | 4/2001 | Vardi et al. |
| 6,210,433 B1 | 4/2001 | Larre |
| 6,249,076 B1 | 6/2001 | Madden et al. |
| 6,254,593 B1 | 7/2001 | Wilson |
| 6,258,115 B1 | 7/2001 | Dubrul |
| 6,258,116 B1 | 7/2001 | Hojeibane |
| 6,261,305 B1 | 7/2001 | Marotta et al. |
| 6,261,316 B1 | 7/2001 | Shaolian et al. |
| 6,264,662 B1 | 7/2001 | Lauterjung |
| 6,264,686 B1 | 7/2001 | Rieu et al. |
| 6,290,673 B1 | 9/2001 | Shanley |
| 6,293,968 B1 | 9/2001 | Taheri |
| 6,325,822 B1 | 12/2001 | Chouinard et al. |
| 6,325,826 B1 | 12/2001 | Vardi et al. |
| 6,334,864 B1 | 1/2002 | Amplatz et al. |
| 6,346,089 B1 | 2/2002 | Dibie |
| 6,355,060 B1 | 3/2002 | Lenker et al. |
| 6,361,544 B1 | 3/2002 | Wilson et al. |
| 6,361,555 B1 | 3/2002 | Wilson |
| 6,379,393 B1 | 4/2002 | Mavroidis et al. |
| 6,383,213 B2 | 5/2002 | Wilson et al. |
| 6,388,043 B1 | 5/2002 | Langer et al. |
| 6,395,018 B1 | 5/2002 | Castaneda |
| 6,436,104 B2 | 8/2002 | Hojeibane |
| 6,436,134 B2 | 8/2002 | Richter et al. |
| 6,508,836 B2 | 1/2003 | Wilson et al. |
| 6,514,237 B1 | 2/2003 | Maseda |
| 6,517,558 B2 | 2/2003 | Gittings et al. |
| 6,520,988 B1 | 2/2003 | Colombo et al. |
| 6,540,779 B2 | 4/2003 | Richter et al. |
| 6,579,309 B1 | 6/2003 | Loos et al. |
| 6,579,312 B2 | 6/2003 | Wilson et al. |
| 6,582,394 B1 | 6/2003 | Reiss et al. |
| 6,596,020 B2 | 7/2003 | Vardi et al. |
| 6,599,316 B2 | 7/2003 | Vardi et al. |
| 6,645,242 B1 | 11/2003 | Quinn |
| 6,679,836 B2 | 1/2004 | Couvillon, Jr. |
| 6,689,156 B1 | 2/2004 | Davidson et al. |
| 6,692,483 B2 | 2/2004 | Vardi et al. |
| 6,695,877 B2 | 2/2004 | Brucker et al. |
| 6,706,062 B2 | 3/2004 | Vardi et al. |
| 6,749,556 B2 | 6/2004 | Banik |
| 6,749,628 B1 | 6/2004 | Callol et al. |
| 6,770,027 B2 | 8/2004 | Banik et al. |
| 6,776,793 B2 | 8/2004 | Brown et al. |
| 6,811,566 B1 | 11/2004 | Penn et al. |
| 6,812,624 B1 | 11/2004 | Pei et al. |
| 6,835,173 B2 | 12/2004 | Couvillon, Jr. |
| 6,835,203 B1 | 12/2004 | Vardi et al. |
| 6,858,038 B2 | 2/2005 | Heuser |
| 6,882,086 B2 | 4/2005 | Kornbluh et al. |
| 6,884,258 B2 | 4/2005 | Vardi et al. |
| 6,896,699 B2 | 5/2005 | Wilson et al. |
| 6,921,360 B2 | 7/2005 | Banik |
| 6,932,837 B2 | 8/2005 | Amplatz et al. |
| 6,940,211 B2 | 9/2005 | Pelrine et al. |
| 6,955,687 B2 | 10/2005 | Richter et al. |
| 6,955,688 B2 | 10/2005 | Wilson et al. |
| 6,962,602 B2 | 11/2005 | Vardi et al. |
| 6,969,395 B2 | 11/2005 | Eskuri |
| 6,982,514 B1 | 1/2006 | Lu et al. |
| 6,997,870 B2 | 2/2006 | Couvillon, Jr. |
| 7,018,400 B2 | 3/2006 | Lashinski et al. |
| 7,056,323 B2 | 6/2006 | Mareiro et al. |
| 7,060,091 B2 | 6/2006 | Killion et al. |
| 7,063,671 B2 | 6/2006 | Couvillon, Jr. |
| 7,771,462 B1 | 8/2010 | Davidson et al. |
| 2001/0003161 A1 | 6/2001 | Vardi et al. |
| 2001/0004706 A1 | 6/2001 | Hojeibane |
| 2001/0004707 A1 | 6/2001 | Dereume et al. |
| 2001/0012927 A1 | 8/2001 | Mauch |
| 2001/0016766 A1 | 8/2001 | Vardi et al. |
| 2001/0016767 A1 | 8/2001 | Wilson et al. |
| 2001/0016768 A1 | 8/2001 | Wilson et al. |
| 2001/0025195 A1 | 9/2001 | Shaolian et al. |
| 2001/0027291 A1 | 10/2001 | Shanley |
| 2001/0027338 A1 | 10/2001 | Greenberg |
| 2001/0029396 A1 | 10/2001 | Wilson et al. |
| 2001/0037116 A1 | 11/2001 | Wilson et al. |
| 2001/0037138 A1 | 11/2001 | Wilson et al. |
| 2001/0039448 A1 | 11/2001 | Dibie |
| 2001/0049552 A1 | 12/2001 | Richter et al. |
| 2001/0056297 A1 | 12/2001 | Hojeibane |
| 2002/0013618 A1 | 1/2002 | Marotta et al. |
| 2002/0013619 A1 | 1/2002 | Shanley |
| 2002/0022874 A1 | 2/2002 | Wilson |
| 2002/0026232 A1 | 2/2002 | Marotta et al. |
| 2002/0035392 A1 | 3/2002 | Wilson |
| 2002/0042650 A1 | 4/2002 | Vardi et al. |
| 2002/0052648 A1 | 5/2002 | McGuckin, Jr. et al. |
| 2002/0054060 A1 | 5/2002 | Schena |
| 2002/0072790 A1 | 6/2002 | McGuckin, Jr. et al. |

| | | | | | |
|---|---|---|---|---|---|
| 2002/0111675 A1 | 8/2002 | Wilson | | FOREIGN PATENT DOCUMENTS | |
| 2002/0156516 A1 | 10/2002 | Vardi et al. | DE | 29701758 | 5/1997 |
| 2002/0156517 A1 | 10/2002 | Perouse | DE | 29701883 | 5/1997 |
| 2002/0165604 A1 | 11/2002 | Shanley | EP | 0347023 | 12/1989 |
| 2002/0173835 A1 | 11/2002 | Bourang et al. | EP | 0479557 | 4/1992 |
| 2002/0173840 A1 | 11/2002 | Brucker et al. | EP | 0479730 | 4/1992 |
| 2002/0183763 A1 | 12/2002 | Callol et al. | EP | 0684022 | 11/1995 |
| 2002/0193735 A1 | 12/2002 | Stiger | EP | 0751752 | 1/1997 |
| 2002/0193872 A1 | 12/2002 | Trout, III et al. | EP | 0783873 | 7/1997 |
| 2002/0193873 A1 | 12/2002 | Brucker et al. | EP | 0804907 | 11/1997 |
| 2003/0009209 A1 | 1/2003 | Hojeibane | EP | 0808140 | 11/1997 |
| 2003/0028233 A1 | 2/2003 | Vardi et al. | EP | 0862392 | 9/1998 |
| 2003/0050688 A1 | 3/2003 | Fischell et al. | EP | 0876805 | 11/1998 |
| 2003/0055378 A1 | 3/2003 | Wang et al. | EP | 0880949 | 12/1998 |
| 2003/0055483 A1 | 3/2003 | Gumm | EP | 0883384 | 12/1998 |
| 2003/0065373 A1 | 4/2003 | Lovett et al. | EP | 0884028 | 12/1998 |
| 2003/0068522 A1 | 4/2003 | Wang | EP | 0891751 | 1/1999 |
| 2003/0074047 A1 | 4/2003 | Richter | EP | 0895759 | 2/1999 |
| 2003/0093109 A1 | 5/2003 | Mauch | EP | 0897700 | 2/1999 |
| 2003/0097169 A1 | 5/2003 | Brucker et al. | EP | 0904745 | 3/1999 |
| 2003/0114912 A1 | 6/2003 | Sequin et al. | EP | 0937442 | 8/1999 |
| 2003/0125791 A1 | 7/2003 | Sequin et al. | EP | 1031328 | 8/2000 |
| 2003/0125802 A1 | 7/2003 | Callol et al. | EP | 1031329 | 8/2000 |
| 2003/0135259 A1 | 7/2003 | Simso | EP | 1031330 | 8/2000 |
| 2003/0181923 A1 | 9/2003 | Vardi | EP | 1070513 | 1/2001 |
| 2003/0195606 A1 | 10/2003 | Davidson et al. | EP | 1157674 | 11/2001 |
| 2003/0236445 A1 | 12/2003 | Couvillon, Jr. | EP | 1190685 | 3/2002 |
| 2004/0006381 A1 | 1/2004 | Sequin et al. | FR | 2678508 | 1/1993 |
| 2004/0015227 A1 | 1/2004 | Vardi et al. | FR | 2740346 | 4/1997 |
| 2004/0044396 A1 | 3/2004 | Clerc et al. | FR | 2756173 | 5/1998 |
| 2004/0059406 A1 | 3/2004 | Cully et al. | GB | 2337002 | 11/1999 |
| 2004/0068161 A1 | 4/2004 | Couvillon, Jr. | WO | WO8806026 | 8/1988 |
| 2004/0087982 A1 | 5/2004 | Eskuri | WO | WO9521592 | 8/1995 |
| 2004/0088007 A1 | 5/2004 | Eidenschink | WO | WO9629955 | 10/1996 |
| 2004/0117003 A1 | 6/2004 | Ouriel et al. | WO | WO9634580 | 11/1996 |
| 2004/0133268 A1 | 7/2004 | Davidson et al. | WO | WO9641592 | 12/1996 |
| 2004/0138732 A1 | 7/2004 | Suhr et al. | WO | WO9707752 | 3/1997 |
| 2004/0143160 A1 | 7/2004 | Couvillon, Jr. | WO | WO9715346 | 5/1997 |
| 2004/0148006 A1 | 7/2004 | Davidson et al. | WO | WO9716217 | 5/1997 |
| 2004/0172121 A1 | 9/2004 | Eidenschink et al. | WO | WO9726936 | 7/1997 |
| 2004/0186560 A1 | 9/2004 | Alt | WO | WO9741803 | 11/1997 |
| 2004/0225345 A1 | 11/2004 | Fischell et al. | WO | WO9745073 | 12/1997 |
| 2004/0267352 A1 | 12/2004 | Davidson et al. | WO | WO9746174 | 12/1997 |
| 2005/0004425 A1 | 1/2005 | Banik | WO | WO9819628 | 5/1998 |
| 2005/0004656 A1 | 1/2005 | Das | WO | WO9836709 | 8/1998 |
| 2005/0010278 A1 | 1/2005 | Vardi et al. | WO | WO9837833 | 9/1998 |
| 2005/0015108 A1 | 1/2005 | Williams et al. | WO | WO9847447 | 10/1998 |
| 2005/0015135 A1 | 1/2005 | Shanley | WO | WO9848879 | 11/1998 |
| 2005/0060027 A1 | 3/2005 | Khenansho et al. | WO | WO9903426 | 1/1999 |
| 2005/0085693 A1 | 4/2005 | Belson et al. | WO | WO9904726 | 2/1999 |
| 2005/0096726 A1 | 5/2005 | Sequin et al. | WO | WO9915103 | 4/1999 |
| 2005/0102017 A1 | 5/2005 | Mattison | WO | WO9915109 | 4/1999 |
| 2005/0102021 A1 | 5/2005 | Osborne | WO | WO9924104 | 5/1999 |
| 2005/0102023 A1 | 5/2005 | Yadin et al. | WO | WO9934749 | 7/1999 |
| 2005/0107669 A1 | 5/2005 | Couvillon, Jr. | WO | WO9936002 | 7/1999 |
| 2005/0119731 A1 | 6/2005 | Brucker et al. | WO | WO9936015 | 7/1999 |
| 2005/0125076 A1 | 6/2005 | Ginn | WO | WO9944539 | 9/1999 |
| 2005/0131526 A1 | 6/2005 | Wong | WO | WO9956661 | 11/1999 |
| 2005/0149161 A1 | 7/2005 | Eidenschink et al. | WO | WO9965419 | 12/1999 |
| 2005/0154442 A1 | 7/2005 | Eidenschink et al. | WO | WO0007523 | 2/2000 |
| 2005/0154444 A1 | 7/2005 | Quadri | WO | WO0010489 | 3/2000 |
| 2005/0165439 A1 | 7/2005 | Weber et al. | WO | WO0016719 | 3/2000 |
| 2005/0183259 A1 | 8/2005 | Eidenschink et al. | WO | WO0027307 | 5/2000 |
| 2005/0187602 A1 | 8/2005 | Eidenschink | WO | WO0027463 | 5/2000 |
| 2005/0209673 A1 | 9/2005 | Shaked | WO | WO0028922 | 5/2000 |
| 2005/0228483 A1 | 10/2005 | Kaplan et al. | WO | WO0044307 | 8/2000 |
| 2006/0036315 A1 | 2/2006 | Yadin et al. | WO | WO0044309 | 8/2000 |
| 2006/0041264 A1 | 2/2006 | Eskuri | WO | WO0047134 | 8/2000 |
| 2006/0041303 A1 | 2/2006 | Israel | WO | WO0048531 | 8/2000 |
| 2006/0079956 A1 | 4/2006 | Eigler et al. | WO | WO0049951 | 8/2000 |
| 2006/0111618 A1 | 5/2006 | Couvillon, Jr. | WO | WO0051523 | 9/2000 |
| 2006/0173528 A1 | 8/2006 | Feld et al. | WO | WO0057813 | 10/2000 |
| 2006/0206188 A1 | 9/2006 | Weber et al. | WO | WO0067673 | 11/2000 |
| 2007/0073376 A1 | 3/2007 | Krolik et al. | WO | WO0071054 | 11/2000 |
| 2007/0112331 A1 | 5/2007 | Weber et al. | WO | WO0071055 | 11/2000 |
| 2007/0208276 A1 | 9/2007 | Volk et al. | WO | WO0074595 | 12/2000 |
| 2007/0250036 A1 | 10/2007 | Volk et al. | WO | WO0121095 | 3/2001 |
| | | | WO | WO0121109 | 3/2001 |

(56) References Cited

FOREIGN PATENT DOCUMENTS

| | | |
|---|---|---|
| WO | WO0121244 | 3/2001 |
| WO | WO0135715 | 5/2001 |
| WO | WO0135863 | 5/2001 |
| WO | WO0139697 | 6/2001 |
| WO | WO0139699 | 6/2001 |
| WO | WO0141677 | 6/2001 |
| WO | WO0143665 | 6/2001 |
| WO | WO0143809 | 6/2001 |
| WO | WO0145594 | 6/2001 |
| WO | WO0145785 | 6/2001 |
| WO | WO0149342 | 7/2001 |
| WO | WO0154621 | 8/2001 |
| WO | WO0154622 | 8/2001 |
| WO | WO0158385 | 8/2001 |
| WO | WO0160284 | 8/2001 |
| WO | WO0170294 | 9/2001 |
| WO | WO0170299 | 9/2001 |
| WO | WO0174273 | 10/2001 |
| WO | WO0189409 | 11/2001 |
| WO | WO0200138 | 1/2002 |
| WO | WO02053066 | 7/2002 |
| WO | WO02068012 | 9/2002 |
| WO | WO03007842 | 1/2003 |
| WO | WO03055414 | 7/2003 |
| WO | WO03063924 | 8/2003 |
| WO | WO2004026174 | 4/2004 |
| WO | WO2004026180 | 4/2004 |
| WO | WO2005009295 | 2/2005 |
| WO | WO2005014077 | 2/2005 |
| WO | WO2006028925 | 3/2006 |

OTHER PUBLICATIONS

Caputo, Ronald P., "Stent Jail: A Minimum-Security Prison," *The American Journal of Cardiology*, vol. 77, pp. 1226-1230 (Jun. 1, 1996).

Carrie, M.D., Didier, "'T'—Shaped Stent Placement: A Technique for the Treatment of Dissected Bifurcation Lesions," *Catheterization and Cardiovascular Diagnosis*, vol. 37, pp. 311-313 (Mar. 1996).

Chevalier, M.D., Bernard, "Placement of Coronary Stents in Bifurcation Lesions by the 'Culotte' Technique," *The American Journal of Cardiology*, vol. 82, pp. 943-949 (Oct. 15, 1998).

Colombo, M.D., Antonio, "'Kissing' Stent for Bifurcational Coronary Lesion," *Catheterization and Cardiovascular Diagnosis*, vol. 30, pp. 327-330 (Dec. 1993).

E. Smela et al., "Thiol Modified Pyrrole Monomers: 1. Synthesis, Characterization, and Polymerization of 1-(2-Thioethyl)-Pyrrole and 3-(2-Thioethyl)-Pyrrole," *Langmuir*, 14 (11), 2970-2975, 1998.

E. Smela, M. Kallenbach, and J. Holdenried, "Electrochemically Driven Polypyrrole Bilayers for Moving and Positioning Bulk Micromachined Silicon Plates," *J. Microelectromechanical Systems*, 8(4), 373-383, 1999.

E.W.H. Jager, E. Smela, O. Inganas, "Microfabricating Conjugated Polymer Actuators," *Science*, 290, 1540-1545, 2000.

Katoh, M.D., Osamu, "New Double Wire Technique to Stent Ostial Lesions," *Catheterization and Cardiovascular Diagnosis*, vol. 40, pp. 400-402 (Apr. 1997).

Lewis, M.D., Bruce E., "Acute procedural results in the treatment of 30 coronary artery bifurcation lesions with a double-wire atherectomy technique for side-branch protection," *American Heart Journal*, vol. 127:6, pp. 1600-1607 (Jun. 1994).

Madden, John D.W. et al., "Polypyrrole actuators: modeling and performance," *Proceedings of the SPIE—Smart Structures and Materials*, vol. 4329 (2001) pp. 73-83.

Nakamura M.D., Shigeru, "Techniques for Palmaz-Schatz Stent Deployment in Lesions With a Large Side Branch," *Catheterization and Cardiovascular Diagnosis*, vol. 34, pp. 353-361 (1995).

Satler, M.D., Lowell F., "Bifurcation Disease: To Treat or Not to Treat," *Catheterization and Cardiovascular Interventions*, vol. 50, pp. 411-412 (2000).

Yamashita, M.D., Ph.D., Takehiro, "Bifurcation Lesions: Two Stents Versus One Stent—Immediate and Follow-up Results," *Journal of the American College of Cardiology*, vol. 35:5, pp. 1145-1151 (Apr. 2000).

ADJUSTABLE BIFURCATION CATHETER INCORPORATING ELECTROACTIVE POLYMER AND METHODS OF MAKINGS AND USING THE SAME

RELATED APPLICATIONS

This application is a continuation of U.S. application Ser. No. 11/591,848, filed Nov. 2, 2006, the entire disclosure of which is incorporated herein by reference.

FIELD OF THE INVENTION

The present invention relates to the field of medical catheters, in particular, medical catheters employing electroactive polymers.

BACKGROUND OF THE INVENTION

Balloon catheters, having expandable balloon members located at the distal end of the balloon catheter, are employed in a variety of medical procedures. These procedures include using balloons as dilatation devices for compressing atherosclerotic plaque which results in a narrowing of the arterial lumen. They also include using balloons for delivery and expansion of prosthetic devices such as stents to a lesion site, i.e., vessel obstruction, within a body vessel.

One medical procedure where balloon catheters are employed is percutaneous transluminal coronary angioplasty, or balloon angioplasty, which is a non-invasive, non-surgical means of treating peripheral and coronary arteries. This technique consists of inserting an uninflated balloon catheter into the affected artery. Dilation of the diseased segment of artery is accomplished by inflating the balloon which pushes the atherosclerotic lesion outward, thereby enlarging the arterial diameter.

In the most widely used form of angioplasty, a balloon catheter is guided through the vascular system until the balloon, which is carried at the distal end of a catheter shaft, is positioned across the stenosis or lesion, i.e., vessel obstruction. An expandable stent can be included on the balloon. The balloon is then inflated to apply pressure to the obstruction whereby the vessel is opened for improved flow. Expansion of the balloon causes expansion of the stent to provide support to the vessel wall.

Within the vasculature, however, it is not uncommon for stenoses to form at a vessel bifurcation. A bifurcation is an area of the vasculature or other portion of the body where a first (or parent) vessel is bifurcated (branched) into two or more branch vessels. Where a stenotic lesion or lesions form at such a bifurcation, the lesion(s) can affect only one of the vessels (i.e., either of the branch vessels or the parent vessel) two of the vessels, or all three vessels. Many prior art stents, however, are not wholly satisfactory for use where the site of desired application of the stent is juxtaposed or extends across a bifurcation in an artery or vein such, for example, as the bifurcation in the mammalian aortic artery into the common iliac arteries.

Desirable characteristics for such assemblies include flexibility and maneuverability for ease of advancement through the body vessel, as well as thin walls and high strength. Furthermore, it is desirable to control dimensional changes in medical balloons including both radial and longitudinal expansion characteristics.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

SUMMARY OF THE INVENTION

At least some embodiments of the invention relate to catheter assemblies, in particular catheter assemblies, for use around vessel bifurcations wherein the assembly comprises one or more regions of electroactive polymer (EAP) to enhance catheter performance. At least one embodiment is directed towards a catheter assembly in which the EAP increases the volume of a portion of the catheter to better address bifurcated geometry. At least one embodiment is directed towards a catheter assembly in which the EAP forms a helix which provides rotational torque to better position the assembly at the bifurcated vessel. At least one embodiment is directed towards an assembly comprising two or more balloon members in which the EAP facilitates coordination of the two or more balloon inflations. At least one embodiment is directed to a catheter assembly, the catheter assembly further comprising a bifurcated stent in which the EAP facilitates fine motion and increased length in the side branch assembly.

These and other aspects, embodiments and advantages of the present invention will be apparent to those of ordinary skill in the art upon review of the Detailed Description and Claims to follow.

DETAILED DESCRIPTION OF THE INVENTION

While this invention may be embodied in many different forms, there are described in detail herein specific embodiments of the invention. This description is an exemplification of the principles of the invention and is not intended to limit the invention to the particular embodiments illustrated.

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

For the purposes of this disclosure, like reference numerals in the figures shall refer to like features unless otherwise indicated.

Depicted in the figures are various aspects of the invention. Elements depicted in one figure may be combined with, or substituted for, elements depicted in another figure as desired.

The present invention relates to the use of electroactive polymer (EAP) actuators embedded within a matrix material which forms at least a portion of a medical device such as a catheter or component thereof. The EAP actuators described herein may be used in any type of medical device, particularly those which are insertable and/or implantable within a body lumen. Specific examples of medical devices where the invention described herein may be employed include catheter assemblies and components thereof which are employed for a variety of medical procedures. Examples of catheter assemblies include, but are not limited to, guide catheters, balloon catheters such as PTA and PTCA catheters for angioplasty, catheters for prostate therapy, TTS endoscopic catheters for gastrointestinal use, single operator exchange or rapid exchange (SOE or RX) catheters, over-the-wire (OTW) catheters, fixed wire catheters, medical device delivery catheters including stent delivery devices in both the self-expanding and balloon expandable varieties, catheters for delivery of vena cava filters, catheters for delivery of percutaneous patent foramen ovale (PFO) closure devices, therapeutic substance delivery devices, thrombectomy devices, endoscopic devices, angiographic catheters, neuro catheters, dilatation catheters, urinary tract catheters, gastrointestinal catheter devices, heat transfer catheters including thermal catheters and cooling, intravascular ultrasound systems, electrophysiology devices, and so on and so forth. The above list is intended for illustrative purposes only, and not as a limitation on the scope of the present invention.

The expandable catheters according to the invention may be actuated, at least in part, with electroactive polymer (EAP) actuators. Electroactive polymers are characterized by their ability to change shape in response to electrical stimulation. EAPs include electric EAPs, ionic EAPs, and piezoelectric material EAPs. Electric EAPs include ferroelectric polymers (commonly known polyvinylidene fluoride and nylon 11, for example), dielectric EAPs, electrorestrictive polymers such as the electrorestrictive graft elastomers and electro-viscoelastic elastomers, and liquid crystal elastomer materials. Ionic EAPs include ionic polymer gels, ionomeric polymer-metal composites, carbon nanotube composites, and liquid crystal elastomer composite materials wherein conductive polymers are distributed within their network structure. Piezoelectric material EAPs may be employed but they tend to undergo small deformations when voltage is applied. The induced displacement of both electronic EAPs and ionic EAPs can be geometrically designed to bend, stretch, contract or rotate.

Ionic EAPs also have a number of additional properties that make them attractive for use in the devices of the present invention. Ionic EAPs, upon application of a small voltage, as small as 1 or 2 volts, and proper design of a substrate, can bend significantly. In addition: (a) they are lightweight, flexible, small and easily manufactured; (b) energy sources are available which are easy to control, and energy can be easily delivered to the EAPS; (c) small changes in potential (e.g., potential changes on the order of 1V) can be used to effect volume change in the EAPs; d) can be used to effect volume change in the EAPs; (e) relatively fast in actuation (e.g., full expansion/contraction in a few seconds); (f) EAP regions can be created using a variety of techniques, for example, electrodeposition; and (g) EAP regions can be patterned, for example, using photolithography, if desired.

Conductive plastics may also be employed. Conductive plastics include common polymer materials which are almost exclusively thermoplastics that require the addition of conductive fillers such as powdered metals or carbon (usually carbon black or fiber).

Ionic polymer gels are activated by chemical reactions and can become swollen upon a change from an acid to an alkaline environment.

Ionomeric polymer-metal composites can bend as a result of the mobility of cations in the polymer network. Suitable base polymers include perfluorosulfonate and perfluorocarboxylate.

Essentially any electroactive polymer that exhibits contractile or expansile properties may be used in connection with the various active regions of the invention, including any of those listed above. The activation of the polymers can be modulated by controlling the electronic pulses with a controlling device. Such modulation allows EAP to perform fine and complicated coordinated motions.

Figure 1A:
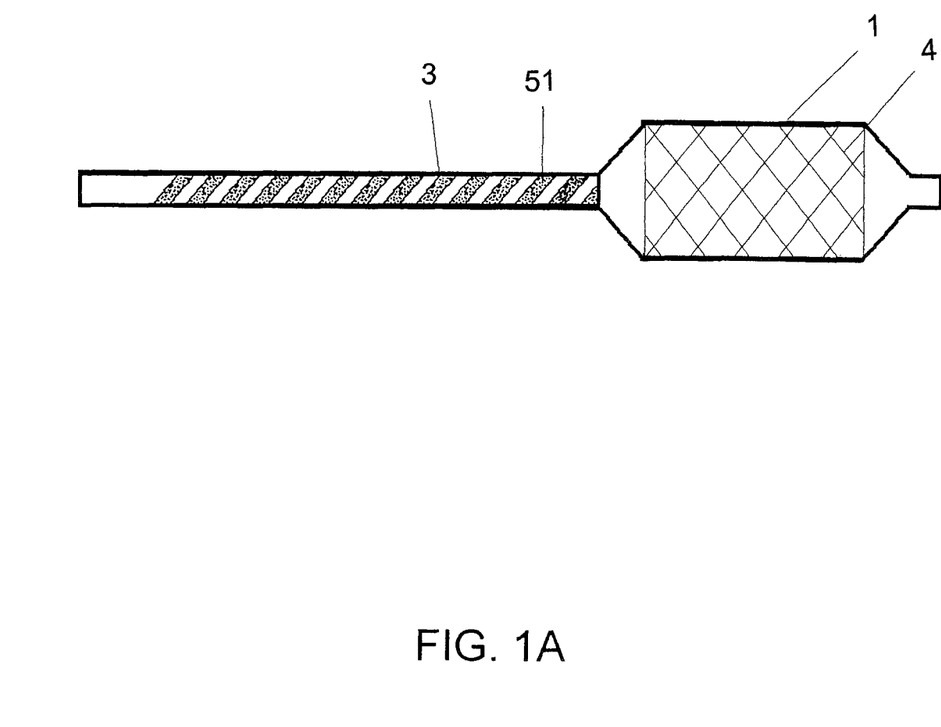
FIG. 1A is an illustration of a stent assembly on a catheter with a stent rotating EAP salient on the catheter.

Referring now to FIG. 1A, there is shown a catheter assembly 1 comprising an implantable catheter 3 including a guidewire lumen sized to advance over a guidewire. The assembly 1 may also include a stent 4, a stent expansion mechanism (including balloons and/or self expanding stent members) emplaced on the catheter 3. The catheter 3 includes an EAP salient or region 51. The salient can be an integrated feature of the catheter or it can be an add-on patch of EAP material. In at least one embodiment, the stent is rotatable relative to the catheter 3 or to at least a portion of the catheter assembly.

The EAP salient has at least two electrical configurations, a first configuration and a second electrical configuration. In at least one embodiment, in the first electronic configuration the salient has a + charge and in the second electronic configuration the salient has a − charge. In at least one embodiment, the first electrical configuration the EAP salient receives a greater electrical charge than in the second. When in the first configuration, the EAP region has a greater volume than when in the second configuration and is referred to as "activated". When activated, the EAP salient 51 can undergo a number of volumetric changes which can move at least a portion of the assembly 1. When the EAP salient is not receiving as great a charge as in the first configuration it is said to be "inactivated" or "deactivated". For purposes of this application, and EAP salient can be said to be "inactivated" and "deactivated" both when it is receiving some electrical current and when it is receiving no electrical current. In at least one embodiment, the EAP salient can also have one or more intermediate configurations. When in one or more intermediate configurations, the EAP salient receives an electrical charge with a voltage less than that of the first configuration and greater than that of the second configuration. By use of multiple intermediate configurations, the EAP salient undergoes intermediate degrees of volumetric change. As a result, controlling the amount of voltage/current received by the EAP salient will allow for a fine degree of control over the EAP induced motion.

In addition to controlling the degree of volumetric change in the EAP salient, the timing of the volumetric change can also be modified. Selecting particular dopants or electrolytes in the EAP salient can adjust the conductivity in the salient. This change in conductivity can slow the reaction times in the salient which will in turn slow the rate of volumetric change. Slow movement by the EAP salient can be used to accurately monitor and adjust catheter alignment.

In at least one embodiment, the EAP salient 51 is in the form of a (primary) helix and winding around the circumference of the catheter 3. When the salient 51 is activated by receiving an electrical pulse the salient 51 increases or reduces its length relative to the shaft of the catheter 3. By extending along the length of the shaft, the helix extends and rotates about the catheter which pushes against both the catheter 3 and the stent. This rotational pushing causes torque which rotates a portion of the assembly 1. In at least one embodiment, a second helix is present and functions as a fine rotation helix. The fine rotation EAP helix is also disposed about the catheter shaft and also has at least two electrical configurations which stimulate changes in volume. The fine rotational helix can be wound in the same or opposite orientation as the primary helix. The volumetric change the fine rotation EAP helix undergoes between its two electrical configurations is designed to be no greater than 30% of the volumetric change of the primary EAP helix allowing for fine modification of the rotational position of the assembly 1.

Although FIG. 1A illustrates the EAP salient as a helix, the salient can be of any shape including a ring around the catheter, a longitudinal or diagonal strip along the catheter or it can be shaped into any other geometric configuration. When the salient is in a non-helical shape, the activation causes the salient to expand against other portions of the assembly and pushing it into some other geometric configuration. All of the EAP pushing mechanisms can be combined with other mechanisms for rotating or moving catheters or other stent components to create highly maneuverable catheter assemblies and stent assemblies.

At least one embodiment involves combining EAP salients with a biased pre-wound catheter. This allows for the catheter 3 to be wound up so as to be biased towards unwinding. The wound up catheter, however, does not unwind because the inactivated EAP salient 51 is configured to restrain the catheter 3 from unwinding. When the EAP is activated, however, the salient moves in such a manner so as to release the restraint and allow the catheter 3 to rotate and unwind. In at least one embodiment, an EAP salient is tightly attached to and wrapped around the catheter shaft forming a tight ring holding the catheter in a wound up state. When activated, however, the salient could either loosen its grip on the catheter allowing it to unwind, or the salient could expand in a circular path in the same direction in which the catheter unwinds which allows the catheter 3 to unwind.

Figure 1B:
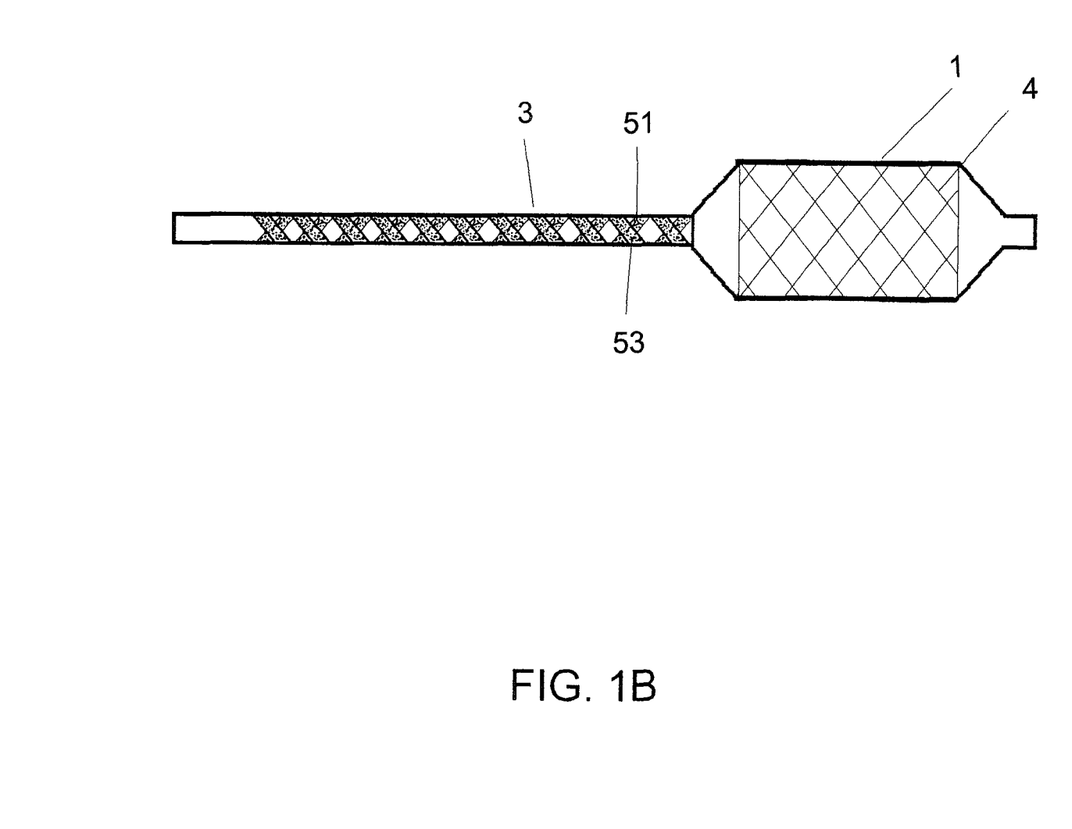
FIG. 1B is an illustration of a stent assembly on a catheter with two stent rotating EAP salients on the catheter.

At least one embodiment as shown in FIG. 1B involves having a second EAP salient 53 also engaged to the catheter 3. Each salient (51 and 53) is positioned in a configuration opposite to the other. In FIG. 1B, the second salient 53 forms a helix winding along a path opposite to that of the first salient 51. The oppositely positioned salient allows for moving an object in the reverse or opposite direction. In the context of FIG. 1B this would mean the stent can be rotated in either a clockwise direction or in a counterclockwise direction. This would allow for last minute adjustments of the stent in the body lumen, for on site correcting of inadvertently misaligned stent positioning, or simply providing the option to rotate the stent in either direction. The positioning of a second EAP salient opposite to a first EAP salient is not limited to application with a helical salient and can be applied to any EAP salient currently disclosed or known in the art.

Figure 2:
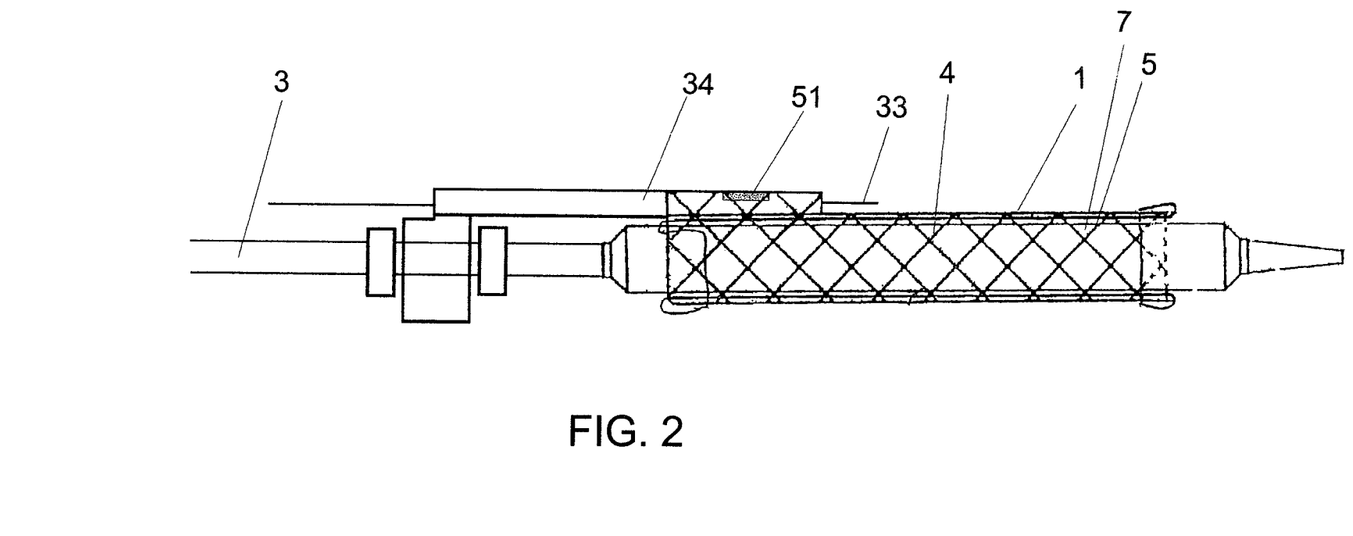
FIG. 2 is an illustration of a stent assembly on a catheter with a side branch guide wire lumen with an EAP salient on the guide wire lumen.
Figure 3:
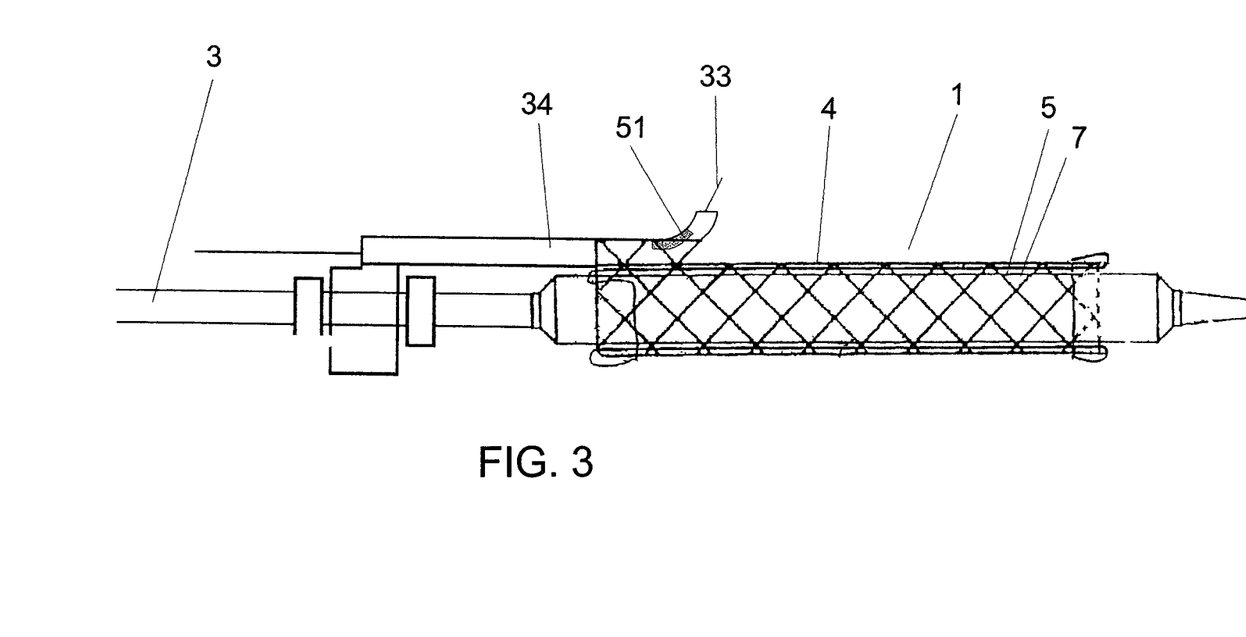
FIG. 3 is an illustration of a stent assembly on a catheter with a side branch guide wire lumen with an EAP salient on the guide wire lumen in which the EAP salient has moved the guide wire lumen.

Referring now to FIG. 2, there is shown an unexpanded catheter assembly 1 having a catheter 3. Attached to the assembly 1 is a secondary lumen or guide wire portal 34 containing a guide wire 33. Such a guide wire 33 is typically fed into a second vessel lumen at a vessel bifurcation. Along the second lumen 34 is an EAP salient 51. Once the catheter reaches the desired location in a body vessel, the current to the salient is reduced which causes the salient to have a shorter length than when activated. As shown in FIG. 3, the salient contraction can contract in a direction generally parallel to the length of the second lumen. This contraction pulls on the second lumen 34 and causes the second lumen to bend or twist away from the catheter assembly 1. In at least one embodiment there can be salients which expand and push the second lumen in the opposite direction.

The EAP guide wire portal can also undergo other changes in response to changing its electrical configurations. In at least one embodiment there is at least a first portal electrical configuration and a second portal electrical configuration. Transitioning between these at least two electrical configurations causes the EAP portal volume to be greater when in the first portal electrical configuration than when in the second portal electrical configuration. The greater volume of the first portal electrical configuration causes a portion of the side branch assembly to be levered open and release the at least one guide wire it is disposed about. The EAP salient 51 can also be designed to hold the wire 33 in place by shaping it in the form of a ring, clamp, opening portal or other attaching geometry holding the wire while in an un-activated state, and to then release the wire upon activation. This also allows for advancement of the device by pushing on the wire which would allow better engagement of the vessel bifurcation.

By placing multiple salients around the second lumen that expand and contract, the second lumen can be pushed and pulled into multiple oblique angles and can be "aimed" into a bifurcated body vessel with a high degree of precision. For purposes of this application, the term "oblique" means an angle between 0 and 180 degrees and explicitly includes 90-degree angles. In addition, there can be at least two EAP regions capable of assuming volumetric changes which push the side branch assembly in opposite directions. These two or more oppositely directed EAP regions can each be linked to one or more independent or linked controller devices capable of coordinating the assumption of the respective electrical configurations of the at least two EAP regions. Oppositely directed EAP regions can allow for motional and counter-motional movement along lateral and rotational vectors, to increase or decrease the depth into the vessel bifurcation a portion of the device will extend, and to change the angle at which the bifurcating portion extends.

In at least one embodiment, by adjusting the number of salients, their position on a catheter assembly, their geometry, and the timing and coordination of their activation or deactivation, a high degree of control over the orientation and positioning of the second lumen 34 or any other portion of the catheter can be achieved. This in turn greatly facilitates the direction of and effectiveness of the guide wire 33 being fed through the second lumen 34 into the vessel bifurcation. In addition, because the salient 51 can bend the second lumen 34 before after and during expansion of the catheter assembly 1, it can be used to both aid in positioning of the unexpanded stent as well as adjusting an expanded stent.

Coordinating the motion of any portion of the catheter assembly can be facilitated by regulating the current released to the various EAP salients by a controller mechanism. This controller mechanism can increase or decrease the voltage causing various EAP salients to expand or contract. The controller mechanism can also be regulated by a computer device or a microchip.

Figure 4:
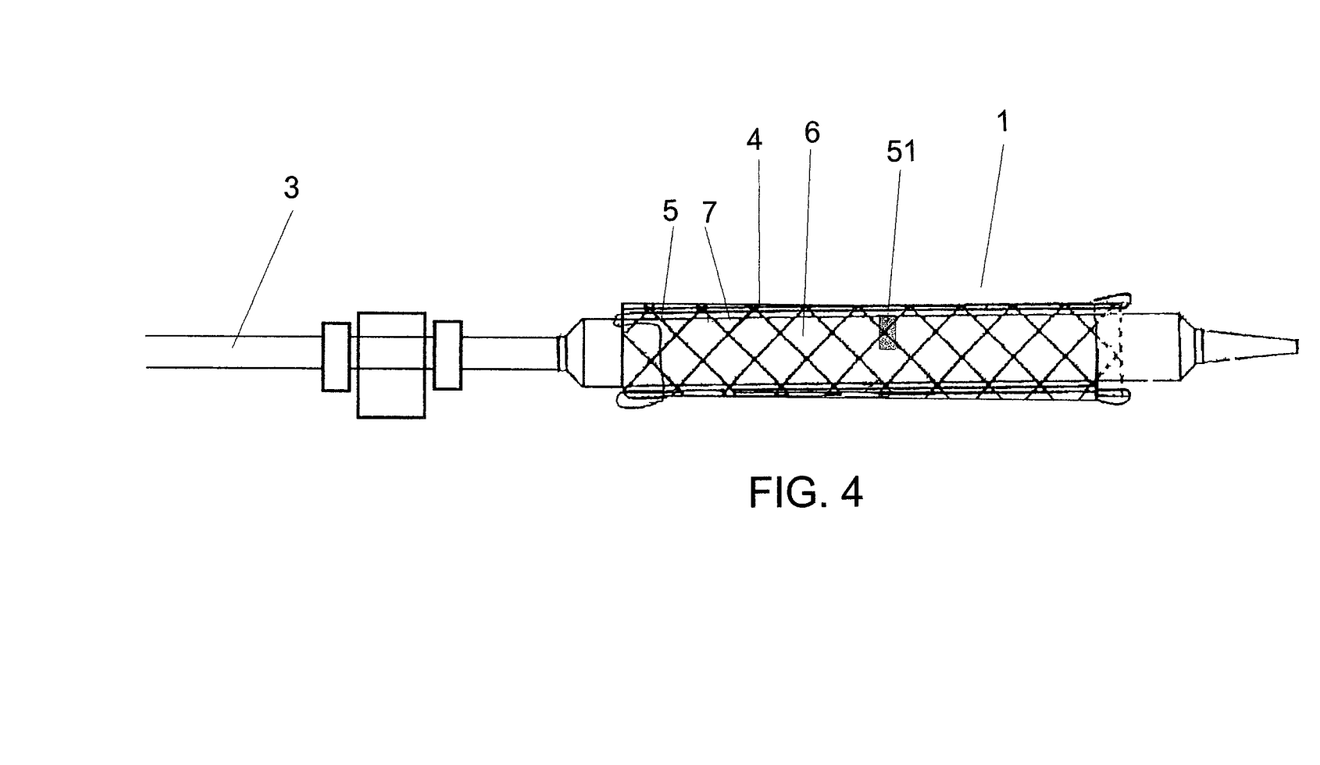
FIG. 4 is an illustration of a stent assembly on a catheter with an EAP salient on the expansion balloon which is capable of rotating or moving the stent.

Referring now to FIG. 4, there is shown a catheter assembly 1 attached to a catheter 3. The catheter assembly includes a balloon 6 for expansion located within a stent 4. Part of the balloon 6 is an EAP salient 51. When activated, the EAP salient 51 expands and presses against the stent 4 exerting a force against the stent 4 which moves the stent 4 relative to the balloon 6. In at least one embodiment, the salient expands in a direction above the circumferential plane of the balloon and at an oblique angle to the catheter towards the stent. By directing how the salient expands, the movement of the stent can be achieved. If the stent 4 is rotatable about the balloon, then extending the salient controls the rotation of the stent. If the stent is not rigidly fixed to a particular point on the catheter, the salient can push the stent in a proximal or a distal direction. The movement capable of implementation by the salient includes lateral movement towards the distal or proximal terminals of the assembly, dorsal movement away from the balloon, rotational movement about the balloon or any combination of these vectors. This allows for increased rotation or positioning of the stent before or after stent deployment and allows for improved "aiming" of the stent at the optimal site on the body vessel for stent deployment.

Figure 5A:
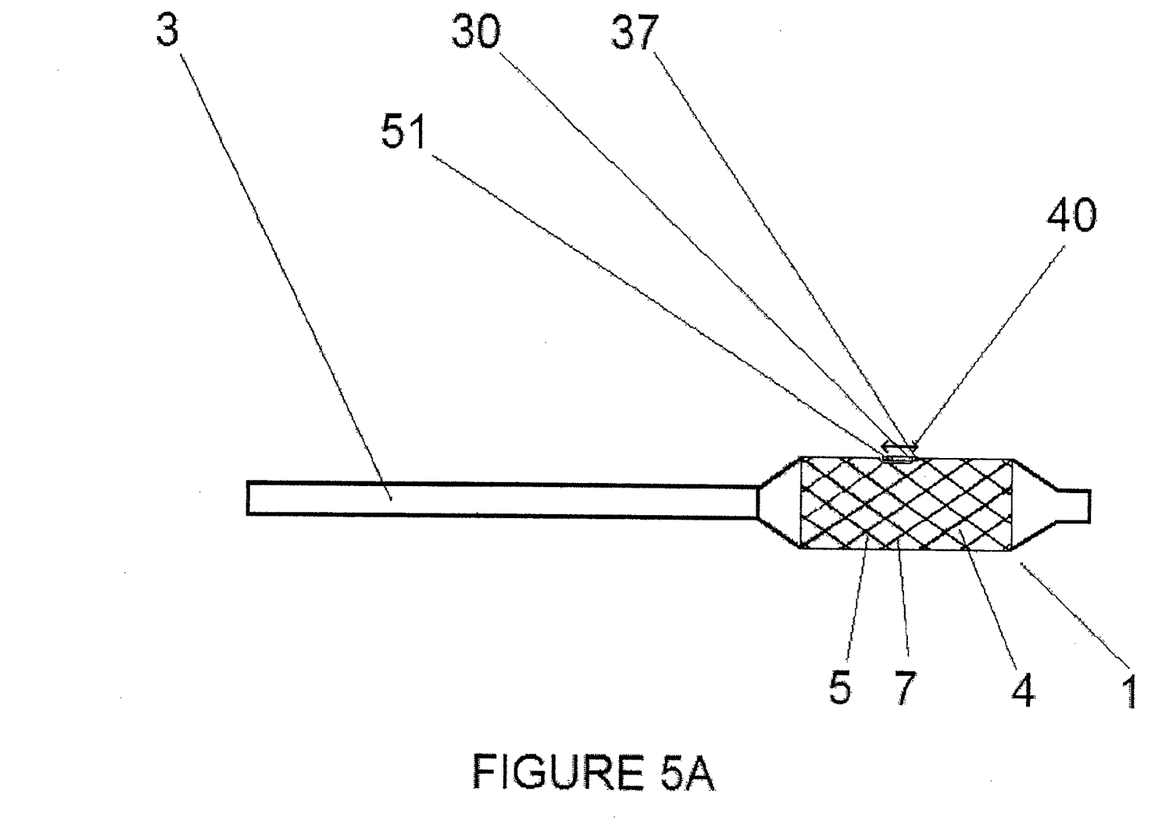
FIG. 5A is an illustration of a catheter assembly with an unbranched and unexpanded bifurcated stent in with an EAP salient on the side branch petals.
Figure 5B:
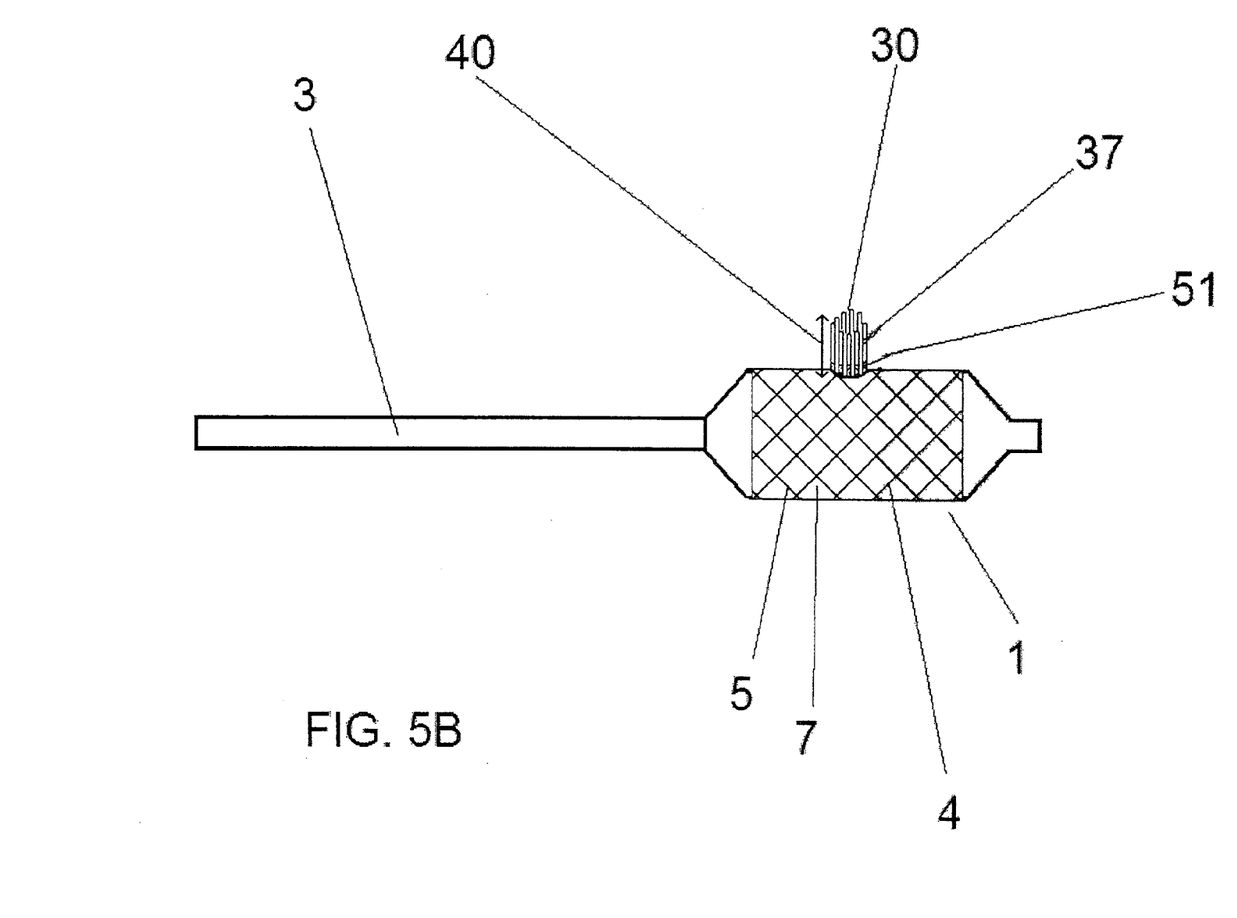
FIG. 5B is an illustration of a catheter assembly with a branched and expanded bifurcated stent in with an EAP salient on the side branch petals.
Figure 5C:
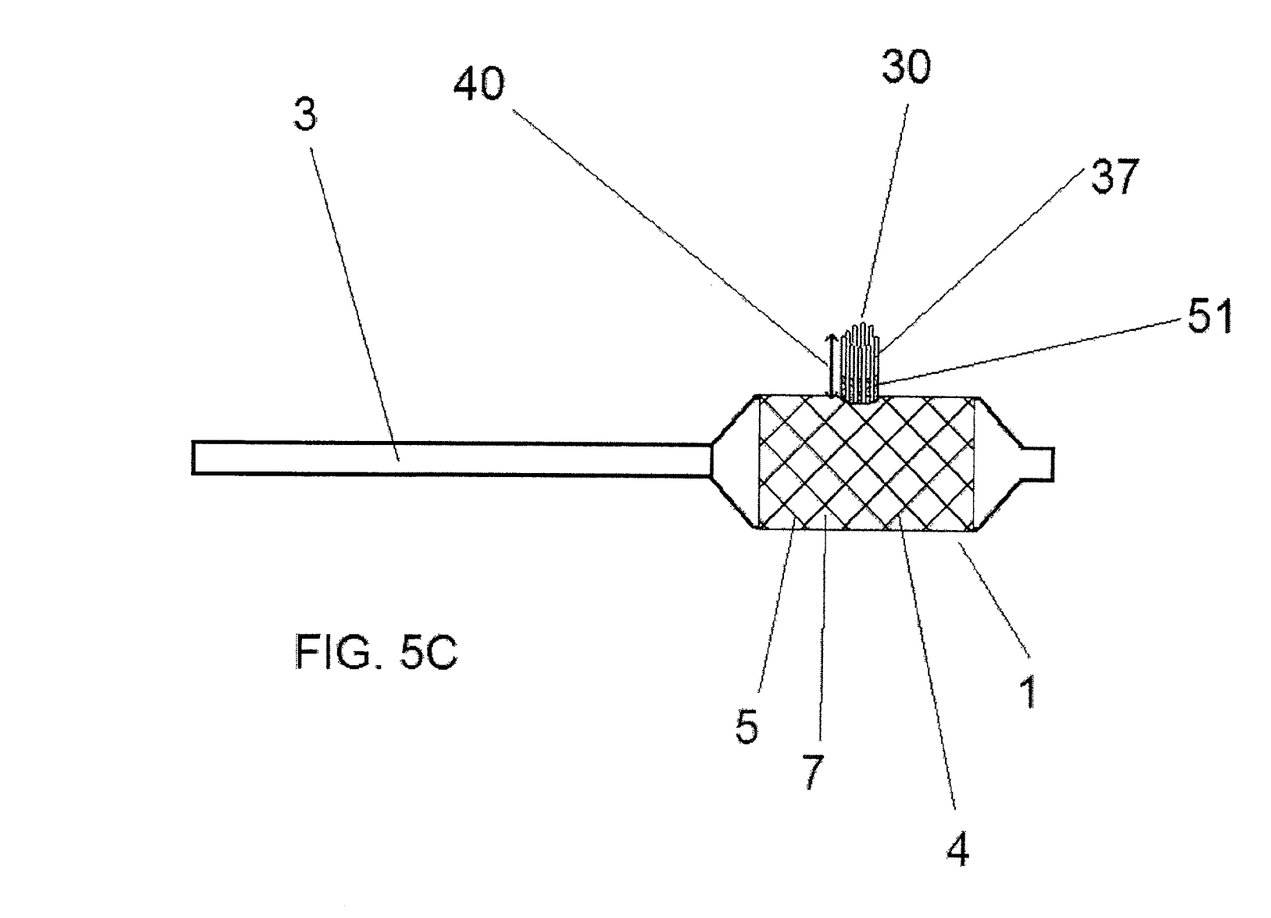
FIG. 5C is an illustration of a catheter assembly with a branched and expanded bifurcated stent in with an EAP salient on the side branch petals in which the EAP salient increases the length of the petals.

Referring now to FIGS. 5A, 5B, and 5C, there are shown bifurcating catheter assemblies 1 featuring a stent with a side branch assembly 30 for extension into a bifurcated body vessel. In FIG. 5A, the catheter assembly 1 is in an unbranched state, and in FIGS. 5B and 5C, the catheter assembly is in a branched state. Although in these illustrations, the side branch assembly 30 comprises petal members 37 capable of defining a second fluid lumen 34, the side branch assembly 30 can be constructed out of any structure including flaps, plates, or any other known shape. Emplaced on at least one of the side branch members 37 is an EAP salient or region 51. FIG. 5A shows that when in the unbranched state, the length 40 of the side branch assembly is generally oriented in a non-oblique configuration relative to the catheter assembly 1 as a whole. In contrast as shown in FIGS. 5B and 5C, when in a branched state, the length 40 of the side branch assembly 30 extends at a significantly more oblique configuration relative to the catheter assembly 1 as a whole. This oblique configuration allows the side branch assembly to extend into a branched body vessel. In the context of this application, the term "oblique" refers to angles of more than 0 and less than 180 degrees and explicitly includes angles of 90 degrees.

In FIG. 5B it is shown that the EAP salient 51 can be positioned along the side branch assembly of either a stent or of the catheter itself. When activated, this salient 51 can facilitate fine and precise movement of the side branch 30. This movement can be used to direct the side branch into difficult-to-fit body vessels, or to improve the positioning or coverage of a deployed bifurcated stent. The salient 51 can precisely push the length 40 into a particular oblique angle relative to the catheter assembly 1 as a whole.

This fine oblique movement can be further facilitated by the structure of the salient 51. As an example, if the salient expands in a direction generally following the length of a member 37, it would push the member to bend and change its angular position. A salient generally following the length of the member 37 could also contract, which would pull on the member and bend it in an opposite direction. In addition, as illustrated in FIG. 5C, the EAP salient 51 in a second electrical configuration could push or pull on a portion of the side branch member to extend along the length 40 of the side branch assembly 30, thus increasing the overall length 40 of the side branch. Such an increase in side branch length 40 would allow the side branch assembly 30 to extend deeper into a branch of a body vessel.

In at least one embodiment, the location of the salient on the member can also affect how it can move the side branch. An expanding salient member located on the distal side (relative to two ends of the stent 4) of a member 37 will bend that member in the proximal direction, and a proximally located expanding salient can push the member in the distal direction. A distally located contracting salient, however, will pull the member towards the distal location, and a proximally located contracting salient will pull the member in the proximal direction. The salients can be designed to push and pull the members in other directions and to position the side branch into extremely oblique angles.

In addition to moving the side branch, EAP salients can also be used to alter the rigidity or flexibility of a portion of the catheter as well as that of the stent. This is possible by taking advantage of the volume change that EAP activation causes. EAP activation can add volume which would increase rigidity, or its deactivation can detract volume and increase flexibility. These volumetric changes can be used to change the size of an inner lumen portion or of a catheter assembly.

The EAP salient can also be used to move some or all of a stent disposed about a catheter relative to the catheter itself. A stent such as a bifurcated stent having a main stent body and at least one projecting member which in an expanded state extends obliquely from the main stent body can be disposed about at least a portion of the catheter. When extended, the at least one projecting member defines a second fluid lumen in fluid communication with the main stent body. In at least one embodiment, when in the first electrical configuration, the EAP region at least partially pushes the at least one projecting member away from the main stent body.

In at least one embodiment, the catheter assembly comprises at least one intermediate electrical configuration which causes the EAP region to assume a volume less than that of the first electrical configuration and greater than that of the second electrical configuration. When in at least one of these intermediate electrical configurations, the change in volume of the EAP region can change how the projecting member of the stent is pushed away from the main stent body. The intermediate configurations can cause one or more projecting members to assume a different oblique angle relative to the main stent body than when in the first electrical configuration or extend to a different distance from the main stent body. Because the intermediate configurations are a result of voltages of intermediate magnitudes, they will usually result in volumetric changes between the minima and maxima (of oblique angle, distance, etc.) of the first and second electrical configurations. In some circumstances, however, geometric constraints or other factors can cause an intermediate voltage level to result in a volumetric change greater or lesser than what is associated with a greater or lesser voltage. In at least one embodiment, at least one projecting member is a petal member as illustrated in FIGS. 5A and 5B.

In addition to locating EAP salients on the side branch of the stent, EAP salients can also be a component of the stent 4. As an example, if the stent 4 comprises a number of struts 5 assembled into columns 7, the EAP salient can cover a strut 5 or at least a portion of a column 7. By attaching EAP to the stent 4, the salient can expand and bend a strut if it overlays a strut. It can also expand and lengthen a member if it is located between rigid strut materials, or it can bend or shorten a strut if a contracting salient is used. At least one embodiment involves having an inactivated EAP salient on a stent 4 which is designed to have a low profile (by having a low volume) during insertion. However, once the stent 4 is located at the deployment site, activating the EAP can increase the volume of the stent 4 providing better body vessel coverage, better structural support, greater lumen volume, greater wall thickness, or improved fluid flow attributes.

Figure 6:
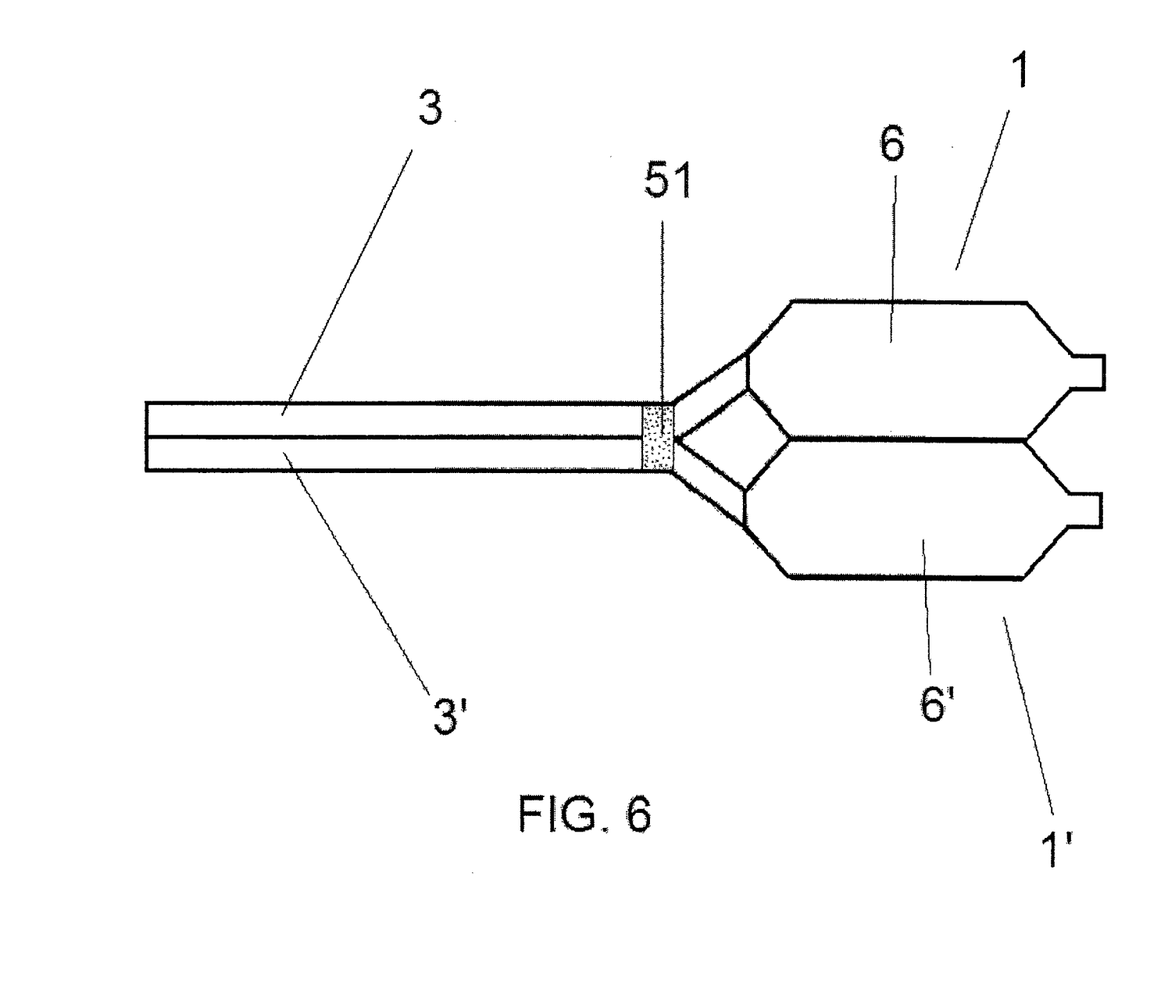
FIG. 6 is an illustration of a dual balloon assembly with an EAP lock holding the balloons together.

Referring now to FIG. 6, there are shown two catheter assemblies 1 having catheters 3 where each catheter has an expansion balloon 6 which abuts the other balloon. This configuration is commonly known as a "kissing balloon" and makes use of the dual balloon expansion for specific stent deployment trajectories. At least one of the catheters 3 has an EAP salient 51. When activated, the salient 51 expands a projecting member which connects the two catheters 3 and restrains the two together. Once the catheters 3 are connected, they can prevent either balloon 6 from pushing the other away from the deployment region and can better assure proper deployment. The EAP salient 51 can be designed to attach and detach as desired and can be designed to move the balloons 6 as well as hold them together.

There are a number of mechanisms by which the EAP salient can bind the two catheters 3 together. In at least one embodiment, one of the catheters 3 has an aperture or opening into which into which either the salient expands or the salient pushes a member which locks the two catheters 3 into place. The opening can be either a blind-hole (a depression with a definite bottom) or a through hole (a cavity which extends completely through the catheter material) as well. The salient could also be designed to loop around or push a member to loop around the other catheter forming a retaining ring. Any other known design for binding two objects could also be utilized to hold the two catheters together.

In some embodiments herein, the EAPs employed are ionic EAPs, more specifically, the ionic EAPs are conductive polymers that feature a conjugated backbone (they include a backbone that has an alternating series of single and double carbon-carbon bonds, and sometimes carbon-nitrogen bonds, i.e., π-conjugation) and have the ability to increase the electrical conductivity under oxidation or reduction. For polymers allows freedom of movement of electrons, therefore allowing the polymers to become conductive. The pi-conjugated polymers are converted into electrically conducting materials by oxidation (p-doping) or reduction (n-doping).

The volume of these polymers changes dramatically through redox reactions at corresponding electrodes through exchanges of ions with an electrolyte. The EAP-containing active region contracts or expands in response to the flow of ions out of, or into, the same. These exchanges occur with small applied voltages and voltage variation can be used to control actuation speeds.

Any of a variety of pi-conjugated polymers may be employed herein. Examples of suitable conductive polymers include, but are not limited to, polypyrroles, polyanilines, polythiophenes, polyethylenedioxythiophenes, poly(p-phenylenes), poly(p-phenylene vinylene)s, polysulfones, polypyridines, polyquinoxalines, polyanthraquinones, poly(N-vinylcarbazole)s and polyacetylenes, with the most common being polythiophenes, polyanilines, and polypyrroles.

Some of the structures are shown below:

Polyaniline          Polypyrrole

Polythiophenes       Polyethylenedioxythiophene

Poly(p-phenylene vinylene)s

Polypyrrole, shown in more detail below, is one of the most stable of these polymers under physiological conditions:

The above list is intended for illustrative purposes only, and not as a limitation on the scope of the present invention.

The behavior of conjugated polymers is dramatically altered with the addition of charge transfer agents (dopants). These materials can be oxidized to a p-type doped material by doping with an anionic dopant species or reducible to an n-type doped material by doping with a cationic dopant species. Generally, polymers such as polypyrrole (PPy) are partially oxidized to produce p-doped materials:

Dopants have an effect on this oxidation-reduction scenario and convert semi-conducting polymers to conducting versions close to metallic conductivity in many instances. Such oxidation and reduction are believed to lead to a charge imbalance that, in turn, results in a flow of ions into or out of the material. These ions typically enter/exit the material from/into an ionically conductive electrolyte medium associated with the electroactive polymer.

Dimensional or volumetric changes can be effectuated in certain polymers by the mass transfer of ions into or out of the polymer. This ion transfer is used to build conductive polymer actuators (volume change). For example, in some conductive polymers, expansion is believed to be due to ion insertion between chains, whereas in others, inter-chain repulsion is believed to be the dominant effect. Regardless of the mechanism, the mass transfer of ions into and out of the material leads to an expansion or contraction of the polymer, delivering significant stresses (e.g., on the order of 1 MPa) and strains (e.g., on the order of 10%). These characteristics are ideal for construction of the devices of the present invention. As used herein, the expansion or the contraction of the active region of the device is generally referred to as "actuation."

The following elements are commonly utilized to bring about electroactive polymer actuation: (a) a source of electrical potential, (b) an active region, which comprises the electroactive polymer, (c) a counter electrode and (d) an electrolyte in contact with both the active region and the counter electrode.

The source of electrical potential for use in connection with the present invention can be quite simple, consisting, for example, of a dc battery and an on/off switch. Alternatively, more complex systems can be utilized. For example, an electrical link can be established with a microprocessor, allowing a complex set of control signals to be sent to the EAP-containing active region(s).

The electrolyte, which is in contact with at least a portion of the surface of the active region, allows for the flow of ions and thus acts as a source/sink for the ions. Any suitable electrolyte may be employed herein. The electrolyte may be, for example, a liquid, a gel, or a solid, so long as ion movement is permitted. Examples of suitable liquid electrolytes include, but are not limited to, an aqueous solution containing a salt, for example, a NaCl solution, a KCl solution, a sodium dodecylbenzene sulfonate solution, a phosphate buffered solution, physiological fluid, etc. Examples of suitable gel electrolytes include, but are not limited to, a salt-containing agar gel or polymethylmethacrylate (PMMA) gel. Solid electrolytes include ionic polymers different from the EAP and salt films.

The counter electrode may be formed from any suitable electrical conductor, for example, a conducting polymer, a conducting gel, or a metal, such as stainless steel, gold or platinum. At least a portion of the surface of the counter electrode is generally in contact with the electrolyte in order to provide a return path for charge.

In at least one embodiment, the EAP employed is polypyrrole. Polypyrrole-containing active regions can be fabricated using a number of known techniques, for example, extrusion, casting, dip coating, spin coating, or electro-polymerization/deposition techniques. Such active regions can also be patterned, for example, using micro extrusion or lithographic techniques, if desired.

As a specific example of a fabrication technique, polypyrrole can be galvanostatically deposited on a platinised substrate from a pyrrole monomer solution using the procedures described in D. Zhou et al., "Actuators for the Cochlear Implant," *Synthetic Metals* 135-136 (2003) 39-40. Polypyrrole can also be deposited on gold. In some embodiments, adhesion of the electrodeposited polypyrrole layer is enhanced by covering a metal such as gold with a chemisorbed layer of molecules that can be copolymerized into the polymer layer with chemical bonding. Thiol is one example of a head group for strong chemisorbtion to metal. The tail group may be chemically similar to structured groups formed in the specific EAP employed. The use of a pyrrole ring attached to a thiol group (e.g., via a short alkyl chain) is an example for a polypyrrole EAP. Specific examples of such molecules are 1-(2-thioethyl)-pyrrole and 3-(2-thioethyl)-pyrrole. See, e.g., E. Smela et al., "Thiol Modified Pyrrole Monomers: 1. Synthesis, Characterization, and Polymerization of 1-(2-Thioethyl)-Pyrrole and 3-(2-Thioethyl)-Pyrrole," *Langmuir*, 14 (11), 2970-2975, 1998.

Various dopants can be used in the polypyrrole-containing active regions including large immobile anions and large immobile cations. According to at least one embodiment, the active region comprises polypyrrole (PPy) doped with dodecylbenzene sulfonate (DBS) anions. When placed in contact with an electrolyte containing small mobile cations, for example, $Na^+$ cations, and when a current is passed between the polypyrrole-containing active region and a counter electrode, the cations are inserted/removed upon reduction/oxidation of the polymer, leading to expansion/contraction of the same. This process can be represented by the following equation:

$$PPy^+(DBS^-)+Na^++e^- \longleftrightarrow PPy^\circ(Na^+DBS)$$

Where Na.sup.+ represents a sodium ion, $e^-$ represents an electron, $PPy^+$ represents the oxidized state of the polypyrrole, $PPy^\circ$ represents the reduced state of the polymer, and species are enclosed in parentheses to indicate that they are incorporated into the polymer. In this case, the sodium ions are supplied by the electrolyte that is in contact with the electroactive polymer member. Specifically, when the EAP is oxidized, the positive charges on the backbone are at least partially compensated by the $DBS^-$ anions present within the polymer. Upon reduction of the polymer, however, the immobile $DBS^-$ ions cannot exit the polymer to maintain charge neutrality, so the smaller, more mobile, $Na^+$ ions enter the polymer, expanding the volume of the same. Upon re-oxidation, the $Na^+$ ions again exit the polymer into the electrolyte, reducing the volume of the polymer.

EAP-containing active regions can be provided that either expand or contract when an applied voltage of appropriate value is interrupted depending, for example, upon the selection of the EAP, dopant, and electrolyte.

Additional information regarding EAP actuators, their design considerations, and the materials and components that may be employed therein can be found, for example, in E. W. H. Jager, E. Smela, O. Inganäs, "Microfabricating Conjugated Polymer Actuators," *Science*, 290, 1540-1545, 2000; E. Smela, M. Kallenbach, and J. Holdenried, "Electrochemically Driven Polypyrrole Bilayers for Moving and Positioning Bulk Micromachined Silicon Plates," *J. Microelectromechanical Systems*, 8(4), 373-383, 1999; U.S. Pat. No. 6,249, 076, assigned to Massachusetts Institute of Technology, and *Proceedings of the SPIE*, Vol. 4329 (2001) entitled "Smart Structures and Materials 2001: Electroactive Polymer and Actuator Devices (see, e.g., Madden et al, "Polypyrrole actuators: modeling and performance," at pp. 72-83), each of which is hereby incorporated by reference in its entirety.

Furthermore, networks of conductive polymers may also be employed. For example, it has been known to polymerize pyrrole in electroactive polymer networks such as poly(vinylchloride), poly(vinyl alcohol), NAFION®, a perfluorinated polymer that contains small proportions of sulfonic or carboxylic ionic functional groups, available from E.I. DuPont Co., Inc. of Wilmington, Del.

Electroactive polymers are also discussed in detail in commonly assigned copending U.S. patent application Ser. No. 10/763,825, the entire content of which is incorporated by reference herein.

In at least one embodiment, the medical devices of the present invention are actuated, at least in part, using materials involving piezoelectric, electrostrictive, and/or Maxwell stresses.

The above disclosure is intended to be illustrative and not exhaustive. This description will suggest many variations and alternatives to one of ordinary skill in this art. All these alternatives and variations are intended to be included within the scope of the attached claims. Those familiar with the art may recognize other equivalents to the embodiments described herein which equivalents are also intended to be encompassed by the claims attached hereto.

The invention claimed is:

1. A device comprising:

a catheter member defining a first guidewire lumen sized to advance over a first guidewire, the catheter member having a longitudinal axis defined along a length of the catheter member; and a guidewire housing member defining a second guidewire lumen sized to advance over a second guidewire and being axially fixed relative to the catheter member, the guidewire housing member having a distal end portion, the distal end portion including at least one activatable material configured to move the distal end portion between at least a first directional arrangement and a second directional arrangement upon application of a stimulus, the first directional arrangement providing a parallel arrangement of the second guidewire relative to the longitudinal axis, and the second directional arrangement providing an angled arrangement of the second guidewire relative to the longitudinal axis.

2. The device of claim 1, wherein the at least one activatable material includes one or more electroactive polymer (EAP) material.

3. The device of claim 1, wherein the guidewire housing member is moveable to at least one intermediate directional arrangement between the first and second directional arrangements.

4. The device of claim 2, wherein the guidewire housing member includes at least two regions of EAP material.

5. The device of claim 4, wherein the at least two regions of EAP material include first and second regions of EAP material positioned on opposite sides of the guidewire housing member.

6. The device of claim 5, wherein the first EAP region contracts to move the guidewire housing member from the first to the second directional arrangement, and the second EAP region expands to move the guidewire housing member from the first to the second directional arrangement.

7. The device of claim 5, wherein the first and second EAP regions are configured to move the guidewire housing member in opposite directions.

8. The device of claim 7, wherein the EAP material in each region is configured to provide a different timing of movement upon application of the stimulus.

9. The device of claim 4, wherein the EAP material in each region is configured to provide a different timing of movement upon application of the stimulus.

* * * * *